United States Patent [19]

Gelfand

[11] Patent Number: 4,631,257
[45] Date of Patent: Dec. 23, 1986

[54] STABLE HIGH COPY NUMBER PLASMIDS

[75] Inventor: David H. Gelfand, Oakland, Calif.

[73] Assignee: Cetus Corporation, Emeryville, Calif.

[21] Appl. No.: 467,369

[22] Filed: Feb. 17, 1983

Related U.S. Application Data

[63] Continuation of Ser. No. 239,165, Feb. 27, 1981, abandoned, and a continuation-in-part of Ser. No. 972,705, Dec. 26, 1978, abandoned.

[51] Int. Cl.[4] .................... C12P 21/00; C12N 15/00; C12N 1/00
[52] U.S. Cl. ................... 435/68; 435/172.3; 435/317; 935/29; 935/42
[58] Field of Search .............. 435/317, 68, 70, 71, 435/172, 172.3; 935/29, 42

[56] References Cited

U.S. PATENT DOCUMENTS 4,237,224 12/1980 Cohen ................................. 435/231

OTHER PUBLICATIONS

Shepard et al., "*Cell*", vol. 18, pp. 267–275, Oct. 1979.
Felipe Cabello, et al., Replication Control in a Composite Plasmid Constructed by in vitro Linkage of Two Distinct Replica, "*Nature*", 259:285–290 (1976).
Barry Polisky, et al., A Plasmid Cloning Vehicle Allowing Regulated Expression of Eukaryotic DNA in Bacteria, "*PNAS*", USA 73:3900–3904 (1976).
Reiner Gentz, et al., Cloning and Analysis of Strong Promoters is Made Possible by the Downstream Placement of a RNA Termination Signal, "*PNAS*", USA 78:4936–4940 (1981).
E. Beck, et al., Nucleotide Sequence of Bacteriophage of DNA, "*Nucleic Acids Research*", vol. 5, No. 12, pp. 4495–4503 (1978).

Primary Examiner—Alvin E. Tanenholtz
Attorney, Agent, or Firm—Albert P. Halluin; Elliott L. Fineman; Virginia Meyer

[57] ABSTRACT

DNA plasmids are described which are selected mutants in which an altered repressor gene leads to high copy number replication. Elements in the plasmids are modified in such a way that readthrough expression of heterologous DNA inserted in the plasmid will not continue into the replication primer strand. Deletions resulting from interference with replication primer strand transcription are thereby avoided.

10 Claims, 4 Drawing Figures

FIG. 2

STABLE HIGH COPY NUMBER PLASMIDS

This is a continuation of application Ser. No. 239,165, filed Feb. 27, 1981, now abandoned, and is a continuation-in-part of Ser. No. 972,705 filed Dec. 26, 1978 now abandoned.

This invention relates to molecular biology and, more particularly to a technique for increasing the levels of expression of protein products encoded by heterologous DNA in cloning vectors.

Genetic change can occur randomly as a result of mutations appearing in a gene. As a result of a change in the gene, a corresponding change may occur in the protein which it encodes, changing the resultant properties of the organism. With the advent of recombinant DNA techniques, such genetic changes may be made deliberately by the introduction of a known nucleotide sequence from one strain or species into another. The known nucleotide sequence may be selected to confer a desired property upon the strain or species into which it is introduced. When the modified strain or species proceeds with the normal replication process, it also then duplicates the inserted sequence.

A commonly used recombinant DNA technique involves breaking open the double-stranded DNA of a plasmid cloning vector at a desired location where foreign DNA is to be inserted. To do this, particular types of proteins, called restriction enzymes, are typically used. Certain restriction enzymes will break the DNA at particular nucleotide sequences. If two different types of DNA are severed in a similar manner, the open ends will therefore be complementary and will, under suitable conditions, stick together with the complementary ends lying side by side. They may then be linked together enzymatically (with ligase). This makes it possible to insert or "splice" a foreign DNA segment from any source into the desired location in the plasmid cloning vector.

All DNA, whether from microbes or from complex plants or animals, consists of the same identical set of nucleotides. Thus, when a DNA fragment derived from a foreign source is spliced into a plasmid, and the plasmid is introduced into a suitable host microorganism, the replication system of the host reproduces the inserted segment along with the DNA of the original host.

Once in the host, the foreign or heterologous DNA is not only replicated from generation to generation, but also will produce protein for which it is encoded. (This assumes the proper reading frame and promoters exist). The amount of protein produced by heterologous DNA as a result of recombination depends, of course, on the magnitude and efficiency of the process used to exploit protein production and replication of the modified host bacteria. Another factor involved in the amount of protein produced is the amount or efficiency of protein production in each bacterium. The proportion of materials produced by heterologous DNA to that produced by the host's own DNA is typically the same from cell to cell and from generation to generation.

Most plasmids exist in only one copy per bacterial cell. Some plasmids, however, exist in higher copy number than one. For example, the plasmid ColEI typically exists in 10 to 20 plasmid copies per chromosome in $E.\ coli$. With certain plasmids it is possible to increase the relative proportion of plasmid DNA in the cell by adding a protein synethesis inhibitor such as chloramphenicol or spectinomycin. Of course, this technique does not assist in the accumulation of protein, if that is what is desired. Because of the presence of inhibitor, only the DNA yield will be higher.

Protein production may be enhanced by the use of so-called super promoters which provide for extremely high levels of protein expression by increasing levels of messenger RNA. Such a technique has limitations, however, in the maximum rate at which the cellular machinery can operate.

Work at the University of California has succeeded in isolating mutants of plasmids wherein copy number is much greater than normal. For example ColEI mutants have been isolated wherein plasmid copy number exceeds 10 to 20 copies per chromosome. However, use of such mutants to produce protein from exogenous DNA may frequently result in failure because of the existence of numerous deletions at important regions in the plasmids.

It is an object of the present invention to provide an improved cloning vector for recombinant DNA production of protein.

Another object of the invention is to provide an improved plasmid capable of existing in high copy number and of giving correct expression of protein.

A further object of the invention is to provide an improved method for obtaining high level protein production from heterologous DNA inserted in plasmid cloning vectors.

Other objects of the invention will become apparent to those skilled in the art from the following description, taken in conjunction with the accompanying drawings wherein:

FIGS. 3 and 4 are schematic diagrams of two forms of plasmids constructed in accordance with the invention.

Figure 1:
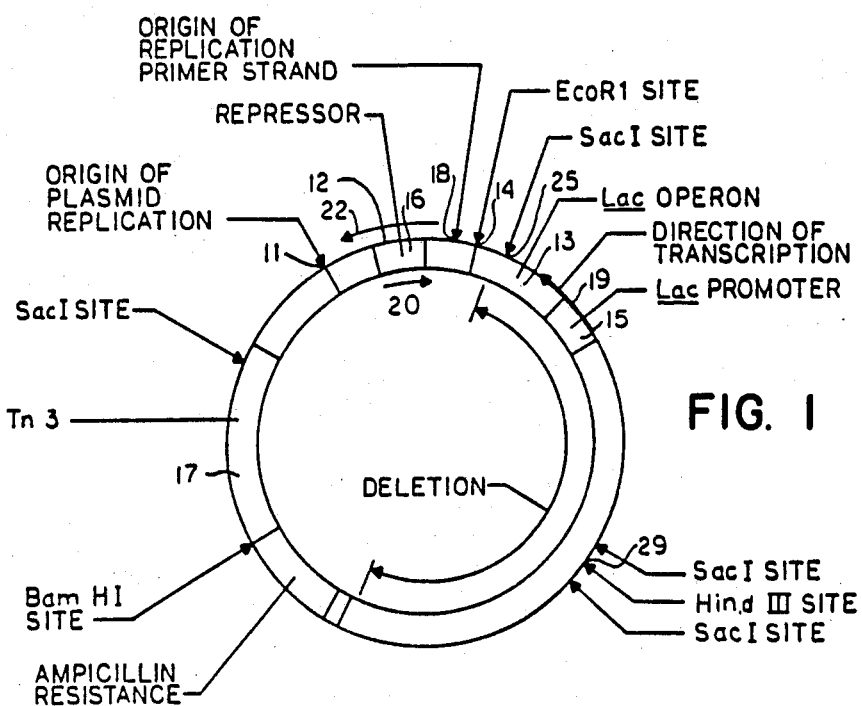
FIG. 1 is a schematic diagram of a plasmid pBGP120.

Very generally, the plasmid of the invention comprises a sequence of DNA containing a site 11 for replication origin, a site 12 for formation of the replication primer strand, a site 13 for the initiation of readthrough expression, and a section 15 of heterologous DNA downstream from and under the control of the expression initiation site and encoded and in the proper reading frame to produce a desired protein. The sequence further has a disabling configuration which prevents readthrough transcription into the replication primer strand gene. The result is a plasmid of high copy number capability which is stable in that deletions are substantially avoided.

In constructing the plasmid of the invention, a plasmid is selected which is useful as a cloning vector. One such plasmid is shown and described in co-pending U.S. patent application Ser. No. 932,429 filed Aug. 9, 1978. This plasmid contains a functional portion of the lac promoter and lac operon indigenous to the host bacteria, terminating in an EcoR1 restriction enzyme site 14 in the beta-galactosidase gene of the lac operon. This portion may be linked at the restriction site 14 to a heterologous gene oriented in the same orientation and having the same reading frame such that readthrough can occur from the lac operon into the heterologous gene in the same reading frame.

This plasmid (pBGP120) exists in high copy number levels, approximately 10 to 20 plasmids per cell chromosome. Plasmids capable of existing at even higher copy numbers are selected by typical prior art techniques. Such techniques include titrating levels of a cloned product produced by the plasmid DNA.

It has been concluded that it is typically a repressor produced by the repressor gene 16 of the plasmid itself which keeps the copy number down, rather than some positive control which provides a stimulus that maintains an elevated copy number. The present invention is preferably applied to a plasmid where a negative control system of this type is present. In this connection, reference is made to the work on PSC101 chimeras by Cabello, et al (1976) Nature 259: 285-290. Typically, several successive screening procedures may be required to select the high copy number mutants. In other words, it is important to the invention that the characteristic of high copy number is indigenous to the plasmid itself, and is not the result of any function uniquely possessed by a particular host bacteria. In any case, the selected plasmid has an altered repressor gene 16' (FIG. 2) leading to high copy number, i.e. in excess of 10–20 per chromosome.

Figure 2:
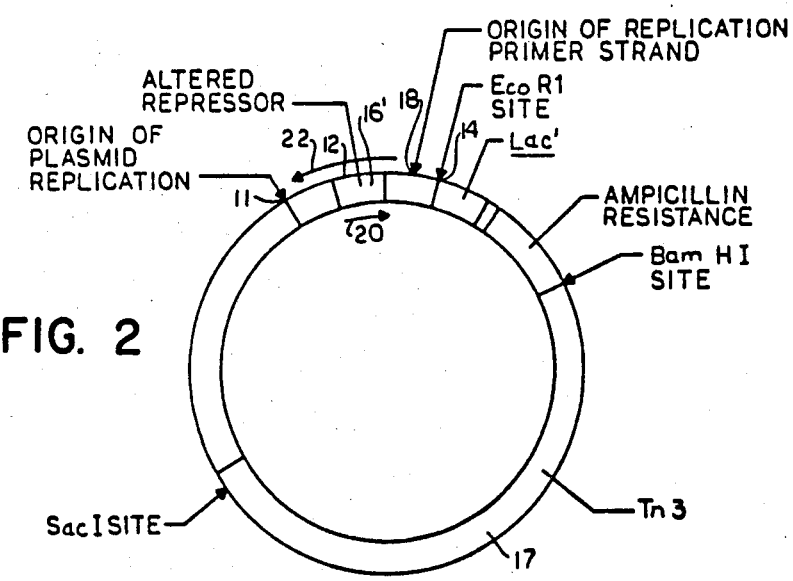
FIG. 2 illustrates a copy number mutant plasmid derived from the plasmid of FIG. 1 wherein a deletion has occurred.
Figure 3:
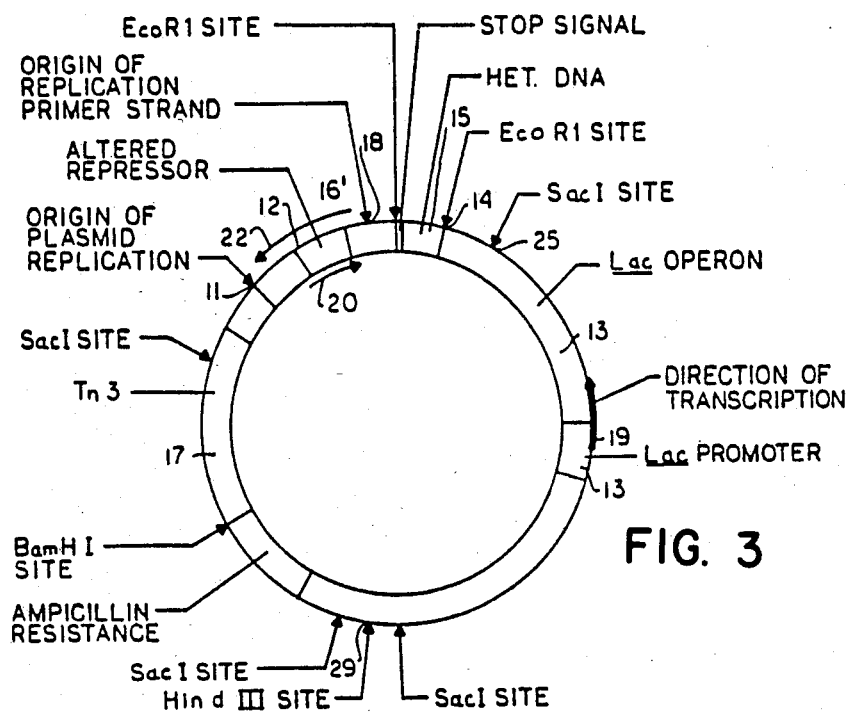

It has been discovered that plasmids thus selected, even though existing in high copy number, almost invariably undergo undesirable deletions of substantial portions of the plasmid (i.e. are unstable). In fact, loss of critical portions of the plasmid, such as the promoter which promotes translation of the inserted heterologous DNA, results in failure of the plasmid to produce the protein desired. The deleted form of the high copy number plasmid is shown in FIG. 2. It may be seen that with the lac promoter and much of the lac operon missing, DNA inserted at the EcoR1 site 14 may be replicated, but transcription can no longer be controller from the lac promoter.

Replication does not begin spontaneously from the origin of plasmid replication 11 shown in FIG. 1. Rather, to begin replication it is necessary for a replication primer RNA strand to be generated. Transcription of this RNA primer strand begins at the origin 18 of the replication primer strand which is located between the EcoR1 site 14 and the repressor 16. It is transcribed counterclockwise on the outer DNA strand 12 and, in the normal situation, stops at the origin of plasmid replication site 11. In reality, however, a large number of RNA primer strands are made which extend beyond the origin site 11. For replication to take place, these RNA primer strands must be processed to trim the strands and delete the extraneous material.

Recent work has shown that the repressor 16 is a segment of RNA which prevents the processing of the RNA replication primer strands to trim the excess RNAs from the strands. Accordingly, replication is unable to originate at the origin site 11. This repressor RNA is made from the inner strand as viewed in FIG. 1 in a clockwise direction, shown by the arrow 20. In the case of the high copy number mutant, this short RNA repressor has a single base mutation which, it may be hypothesized, prevents the folding of the repressor RNA in such a way as to block the processing of the excessively long primer strands.

In such high copy number mutants, it is postulated that deletions in the plasmids occur as a result of readthrough transcription initiated from the lac promoter (under cyclic AMP control) in a counterclockwise direction as viewed in FIG. 1 into and through the replication primer strand. The cell either loses the plasmid by not replicating it or the cell turns off the lac promoter by appropriate deletions.

The direction of transcription of the lac promoter is shown in FIGS. 1, 4 and 5 by the arrow 19. The transcription of the primer strand is in the same direction as lac and is shown by the arrow 22. Copy number alone is not enough to produce the instability, because the mutant is quite stable (i.e. full size) in cells where low levels of lac transcription occur.

So, with the above model in mind, several approaches can be utilized to generate stable, full-sized mutants. One method is to terminate readthrough transcription from the lac operon by placing a suitable transcriptional "stop" signal after the inserted heterologous gene. This can be done using known techniques with an appropriate restriction enzyme and ligase.

Another approach will also stabilize the high copy number mutant. As set forth above, the reason that transcription of the replication primer strand is interfered with is readthrough transcription from the lac promoter. This second approach, therefore, is to turn the lac promoter around so that it transcribes away from the replication primer strand region.

Referring to FIG. 1, it may be seen that the lac operon is bracketed by EcoR1 and HinDIII sites 14 and 29, respectively. The plasmid pBGP120 is cut by these two enzymes and fragments separated by size. The selected lac fragment is now mixed with HinDIII-EcoR1 bifunctional linkers Bahl et al. *Biochemical and Biophysical Research Communications*, 81: 695-703 (April 1978). As is known, these linkers have an open HinDIII site at one end and an open EcoR1 site at the other. A certain percentage of the time, one linker will attach itself to each end of the lac fragment, ligated into place covalently. This fragment can now be reconnected to the other plasmid fragment and those plasmids selected where the reconnected fragments have the desired opposite orientation. Transcription is now away from the primer site. Thus, the plasmid is stable.

One further change is required to insert the heterologous DNA. It may be seen that the above-described reversal will leave two EcoR1 sites at each end (and two HinDIII sites as well). Unwanted EcoR1 sites (and HinDIII sites) may be removed by appropriate known techniques, such as partial digestion of the DNA followed by exonuclease treatment (Polisky et al; Proc. Nat'l. Acad. Sci. 73: 3900-3904). These plasmids may now be screened for high copy number mutants.

It is useful to have temperature-sensitive (Ts) copy number mutants. That is because high level production of some protein products of heterologous DNA may have a deleterious effect on the host cells. In temperature-sensitive copy number mutants, there is a maintenance of low copy number when the host cells are grown at a "permissive" temperature (usually relatively lower). When the product of the heterologous DNA is desired in quantity, the temperature is shifted (usually increased). At this non-permissive or restrictive temperature, the mutation manifests itself and the plasmid copy number increases, resulting in increased protein production from the plasmids.

Such Ts mutants are rare, but can be found for almost any type of mutant by appropriate selection. First the location of the copy number mutant is determined by fine-mapping with genetic recombination. Once the location is known, the spot is specifically mutagenized. This can be done by nucleotide alteration or by cutting out the region with restriction enzymes, strongly mutagenizing the fragment with some agents such as bisulfite, hydroxylamine or ultraviolet radiation, and replacing the fragment. The resultant plasmids are transformed into cells that overproduce lac repressor. These are then plated over Xgal at permissive temperatures. Blue regions are removed from the culture. Then, at elevated temperatures, new blue areas that appear are temperature-sensitive mutants which are picked.

These mutations are generally "recessive in trans.". That means, when a mutant and a normal plasmid are put in the same cell, the altered or "high copy number phenotype" is masked.

The deleted form of the copy number mutant can exist in the same cell as the normal copy number parental-type plasmid. (This is not true of the non-mutant because of the property of incompatibility. In spite of the similar mode of replication, this property is not manifested with the deleted form). When they are placed in the same cell, the copy number of both types of plasmids falls to normal (10-15). Thus, it can be concluded that a diffusable product—the repressor—normally maintains the low copy number, but is absent or inactive in mutant form.

However, it is useful to have a copy number mutant that is dominant in trans. This allows a more generalized approach in that non-copy number mutant plasmids with similar modes of replication can be grown to a high copy level in hosts carrying such a trans-dominant mutation.

It may be seen, therefore, that the invention provides an improved plasmid capable of existing and replicating in high copy number and of giving correct expression of protein. By high copy number, it is meant typically in excess of fifty plasmids per chromosome and preferably in the range of one hundred to five hundred or greater. The plasmid thus enables one to obtain very high level production of protein from heterologous DNA.

Various modifications of the invention in addition to those shown and described herein will become apparent to those skilled in the art from the foregoing description and accompanying drawings. Such modifications are intended to fall within the scope of the appended claims.

What is claimed is:

1. A DNA plasmid comprising, a site for replication origin, a gene for formation of a replication primer strand, a site for the initiation of readthrough expression, a section of heterologous DNA downstream from said expression initiation site encoded and in proper reading frame to produce a desired protein, and an altered repressor gene leading to high copy number replication, said plasmid further having a disabling configuration for preventing readthrough transcription into said gene for the replication primer strand, said disabling configuration comprising said expression initiation site and said heterologous DNA oriented so that transcription thereof occurs oppositely to the direction of transcription of said replication primer strand gene or a stop sequence interposed between said heterologous DNA and said replication primer strand gene or both.

2. A plasmid according to claim 1 wherein said repressor gene is altered in such a way as to produce defective repressor.

3. A plasmid according to claim 1 wherein said repressor gene is altered in such a way as to produce no repressor.

4. A plasmid according to claim 1 wherein said expression initiation site comprises a site for the initiation of translation and at least a substantial portion of a gene which is indigenous to the host species of bacteria whereby readthrough can occur from said indigenous gene portion into said heterologous DNA.

5. A plasmid according to claim 1 having a high copy number mutant repressor gene which is temperature-sensitive.

6. A method for producing protein in a host microorganism, which protein is encoded by heterologous DNA, said method comprising utilizing a host microorganism containing plasmids in higher than normal copy number, each of said plasmids comprising, a site for replication origin, a site for formation of a replication primer strand, a site for the initiation of readthrough expression, a section of heterologous DNA downstream from said expression initiation site encoded and in proper reading frame to produce a desired protein, and an altered repressor gene leading to high copy number replication, said plasmid further having a disabling configuration for preventing readthrough transcription into said site for the replication primer strand, said disabling configuration comprising said expression initiation site and said heterologous DNA oriented so that transcription thereof occurs oppositely to the direction of transcription of said replication primer strand site, or a stop sequence interposed between said heterologous DNA and said replication primer strand or both.

7. A method according to claim 6 wherein said repressor gene is altered in such a way as to produce defective repressor.

8. A method according to claim 6 wherein said repressor gene is altered in such a way as to produce no repressor.

9. A method according to claim 6 wherein said expression initiation site comprises a site for the initiation of translation and at least a substantial portion of a gene which is indigenous to the host species of bacteria whereby readthrough can occur from said indigenous gene portion into said heterologous DNA.

10. A method according to claim 6 having a high copy number mutant repressor gene which is temperature-sensitive and trans-dominant.

* * * * *